United States Patent
Olree et al.

(10) Patent No.: US 8,834,341 B2
(45) Date of Patent: Sep. 16, 2014

(54) COIL OPTIMIZATION FOR MAGNETIC STIMULATION

(76) Inventors: Kenneth Stephen Olree, Searcy, AR (US); Kenneth W. Horch, Fountain Hills, AZ (US)

( * ) Notice: Subject to any disclaimer, the term of this patent is extended or adjusted under 35 U.S.C. 154(b) by 2168 days.

(21) Appl. No.: 11/743,382

(22) Filed: May 2, 2007

(65) Prior Publication Data

US 2008/0275289 A1   Nov. 6, 2008

(51) Int. Cl.
*A61N 2/02* (2006.01)
*G06F 17/50* (2006.01)
*H01F 7/20* (2006.01)
*A61N 2/00* (2006.01)

(52) U.S. Cl.
CPC ............ *G06F 17/5009* (2013.01); *H01F 7/202* (2013.01); *A61N 2/006* (2013.01); *A61N 2/02* (2013.01); *G06F 2217/06* (2013.01)
USPC .......................................................... 600/13

(58) Field of Classification Search
CPC ........... A61N 2/02; A61N 1/40; A61N 2/006; A61N 1/37229; A61B 5/055; A61B 5/06; G01R 33/287
USPC ...................... 600/9–15, 417; 335/299; 607/2
See application file for complete search history.

(56) References Cited

U.S. PATENT DOCUMENTS

2003/0073899 A1*   4/2003   Ruohonen et al. ............ 600/417

OTHER PUBLICATIONS

Lin, V.W. et al., "Functional magnetic stimulation for restoring cough in patients with tetraplegia," *Arch. Phys. Med. Rehabil.*, vol. 79, No. 5, pp. 517-522, May 1998.
Lin, V.W. et al., "Magnetic coil design considerations for funcitional magnetic stimulation," *IEEE Trans. Biomed. Eng.*, vol. 47, No. 5, pp. 600-610 May 2000.
Mills, K.R., *Magnetic stimulation of the human nervous systems*, New York, Oxford University Press, 1999, ch. 8-18, pp. 168-322.
Nielsen, J.F., et al., "Treatment of spasticity with repetitive magnetic stimulation; a double-blind placebo-controlled study," *Mult. Scler.*, vol. 2, No. 5, pp. 227-232, Dec. 1996.
George. M.S. et al. "Daily repetitive transcranial magnetic stimulation (rTMS) improves mood in depression," *Neuroreporter*, vol. 6, No. 14, pp. 1853-1856, Oct. 1995.

(Continued)

*Primary Examiner* — Christine Matthews
(74) *Attorney, Agent, or Firm* — Foley & Lardner LLP

(57) ABSTRACT

A method of determining an optimal coil shape for use in magnetic stimulation includes identifying a stimulation location and a constraint at the stimulation location. A first electromagnetic effect at the stimulation location is determined. The first electromagnetic effect is induced by a first electrical quantity assigned to a first current element at a first current element location with a first orientation. A second electromagnetic effect at the stimulation location is also determined. The second electromagnetic effect is induced by a second electrical quantity assigned to a second current element at the first current element location with a second orientation. Based on the first electromagnetic effect and the second electromagnetic effect, an optimal orientation of a current element at the first current element location is determined. The optimal orientation is such that the constraint is satisfied. Repeating the process at a plurality of locations yields the optimal coil shape.

25 Claims, 6 Drawing Sheets

(56) References Cited

OTHER PUBLICATIONS

Carbunaru, R. and Durand, D.M., "Toroidal coil models for transcutaneous magnetic stimulation of nerves," *IEEE Trans. Biomed Eng.*, vol. 48, No. 4, pp. 434-441. Apr. 2001.

Cohen, L.G. et al., "Effects of coil design on delivery of focal magnetic stimulation. Technical considerations," *Electroencephalogr. Clin. Neurophysiol.*, vol. 75, No. 4, pp. 350-357, Apr. 1990.

Cohen, D. et al., "Developing a more focal magnetic stimulator. Part I: Some basic principles," *J. Clin. Neurophysiol.*, vol. 8, No. 1, pp. 102-111, Jan. 1991.

Basser, P.J., "Focal magnetic stimulation of an axon," *IEEE Trans. Biomed. Eng.*, vol. 41, No. 6, pp. 601-606, Jun. 1994.

Zimmerman, K.P. et al., "Slinky coils for neuromagnetic stimulation," *Electroencephalogr. Clin. Neurophysiol.*, vol. 101, No. 2, pp. 145-152, Apr. 1996.

D'Inzeo, G. et al., "Comparison of homogenous and heterogeneous tissue models for coil optimization in neural stimulation," *Radio Sci.*, vol. 30, No. 1, pp. 245-253, Feb. 1995.

Hsiao, I.N. et al., "Improved coil design for functional magnetic stimulation of expiratory muscles," *IEEE Trans. Biomed. Eng.*, vol. 48 No. 6, pp. 684-694, Jun. 2001.

Odagaki, M. et al., "Study on optimization for current distribution in magnetic stimulation therapy for urinary incontinence," *Neurol. Clin. Neurophysiol.*, vol. 44, pp. 1-5, Nov. 2004.

Roth, Y. et al., "A coil design for transcranial magenetic stimulation of deep brain regions," *J. Clin. Neurophysia*, vol. 19, No. 4, pp. 361-370, Aug. 2002.

Epstien, C.M. et al., "Iron-core coils for transcranial magnetic stimulation," *J. Clin. Neurophysiol.*, vol. 19, No, 4, pp. 376-381, Aug. 2002.

Nadeem, M. et al., "Computation of electric and magnetic stimulation in humean head using the 3-D impedance method," *IEEE Trans. Biomed. Eng.*, vol. 50, No. 7, pp. 900-907, Jul. 2003.

Ruohonen, J. et al., "Coil optimization for magnetic brain stimulation," *Ann Biomed. Eng.*, vol. 25, No. 5, pp. 840-849, Oct. 1997.

Ruohonen, J. et al., "Functional magnetic stimulation: theory and coil optimization," *Bioelectrochem. Bioenerg.*, vol. 47, No. 2, pp. 213-219, Dec. 1998.

Nagarajan, S.S. et al., "Effects of induced electric fields on finite neruronal structures: a simulation study," *IEEE Trans. Biomed. Eng.*, vol. 40, No. 11, pp. 1175-1188, Nov. 1993.

Gandhi, O.P. et al., "Impedance method for calculation of power deposition patterns in magnetically induced hyperthermia," *IEEE Trans. Biomed. Eng.*, vol. 31, No. 10, pp. 644-651, Oct. 1984.

Orcutt, N. et al., "A 3-D impedance method to calculate power desposition in biological bodies subjected to time varying magnetic fields," *IEEE Trans. Biomed. Eng.*, vol. 35, No. 8, pp. 577-583, Aug. 1988.

Stuckly, M.A. et al., "Modeling induced currents in biological cells exposed to low-frequency magnetic fields," *Phys. Med. Biol.*, vol. 39, No. 9, pp. 1319-1330, Sep. 1994.

Stuchly, M.A. et al., "Magnetic field-induced currents in the human body in proximity of power lines," *IEEE Trans. Power Delivery*, vol. 11, No. 1, pp. 102-109, Jan. 1996.

Ghandi, O.P. et al., "Calculation of induced current densities for humans by magnetic fields from electronic article surveillance devices," *Phys. Med. Biol.*, vol. 46, No. 11, pp. 2759-2771, Nov. 2001.

Kang, G. et al., "Comparison of various safety guidelines for electronic article surveillance devices with pulsed magnetic fields," *IEEE Trans. Biomed. Eng.*, vol. 50, No. 1 pp. 107-113, Jan. 2003.

Olree, K.S. et al., "Differential activation and block of peripheral nerve fibers by magnetic fields," *Muscle Nerve*, vol. 34, No. 2, 189-196, Aug. 2006.

Andreucetti, D. et al., "Dielectric properties of body tissues," [Internet], Florence (Italy): Italian National Research Council, Institute for Applied Physics Nello Carrara. [cited Sep. 16, 2006]. Available form: http://niremf.ifac.cnr.it/tissprop/htmlclie.html.

Heath, M. *Scientific computing: an introductory survey*, New York, McGraw-Hill, 1997, ch. 7, pp. 226-227.

Tuday, E.C. et al., "Differential activation of nerve fibers with magnetic stimulation in humans," *BMC neurosci.*, 2006 7:58.

Heath, M. *Scientific computing and introductory survey*, New York, McGraw-Hill, 1997, ch. 2, pp. 54-59.

* cited by examiner

COIL OPTIMIZATION FOR MAGNETIC STIMULATION

FIELD

The subject of the disclosure relates generally to a method of determining an optimal shape of a magnetic coil for use in delivery of magnetic energy. More specifically, the disclosure relates to a method of determining an optimal shape of a magnetic coil by using Lagrange multipliers to ensure that the magnetic coil is globally optimal and capable of simultaneously stimulating a plurality of stimulation locations.

BACKGROUND

Magnetic stimulation has been used extensively for researching and treating a large number of clinical conditions. Magnetic stimulation can be implemented by passing a time varying current through a coil. As known to those skilled in the art, the time varying current creates a time varying magnetic field in the area near the coil. By placing the coil near or in contact with a patient, the time varying magnetic field passes through at least a portion of the patient. The time varying magnetic field induces an electrical field which in turn causes an electrical current (or eddy current) within the patient. The eddy current interacts with and is capable of stimulating the patient's neural tissue. For example, if the electrical field has a large negative gradient of sufficient duration, it can cause nerve fibers in the patient to depolarize and initiate an action potential. If the electrical field has a large positive gradient, it can cause nerve fibers to hyperpolarize, and may even be able to block action potential propagation.

Magnetic stimulation is similar to electrical stimulation in that both use a current to stimulate a patient's neural tissue. However, magnetic stimulation has several advantages over electrical stimulation. Magnetic stimulation is relatively painless and can easily be applied through an electrically insulated portion of the patient, such as a skull. Further, magnetic stimulation does not require an invasive procedure, and if the magnetic stimulator is powerful enough, magnetic stimulation may not even require contact with the patient.

A major limitation of magnetic stimulation is the ability to design a coil that is capable of efficiently inducing a desired electric field or other constraint at a specified stimulation location within a patient or other individual. It is desirable that the induced electric field be controlled, for example, such that stimulation takes place at the stimulation location and does not interfere with or excite any neighboring locations within the patient.

Many researchers have conducted optimization studies in an attempt to optimize coil designs to improve the ability to control the stimulus location for magnetic stimulation of both the central and peripheral nervous systems. These optimization studies have examined maximizing the electric field or the electric field gradient for various tissues by altering coil shapes, sizes, orientations, number of coils used, etc. A major problem of coil designs generated based on these optimization studies is that they assume a general (round or elliptical) shape of the optimal coil and then alter a limited number of parameters affecting the assumed shape in an attempt to achieve a stimulation goal. Because the general shape is assumed and not determined, there is no guarantee that the coil design found is globally optimal. In addition, traditional magnetic stimulation coils have been designed without considering the effects of heterogeneity of the conductivity of surrounding tissues. Further, traditional magnetic stimulation coils are limited in their ability to effectively control the magnetic stimulation at more than one location.

Thus, there is a need for an optimization technique which can be used to determine an optimal coil shape for a magnetic stimulation device such that desired objectives can be realized. Further, there is a need for an optimization technique to determine an optimal coil solution in which the general coil shape is not assumed. Further, there is a need for an optimization technique for determining a coil which considers the heterogeneity of the conductivity of tissues surrounding a desired tissue location. Further, there is a need for an optimization technique to determine an optimal coil shape such that a desired electric field profile can be simultaneously provided to a plurality of tissue locations.

SUMMARY

An exemplary method of determining an optimal magnetic coil shape for use in magnetic stimulation is provided. A stimulation location and a constraint at the stimulation location are identified. A first electromagnetic effect at the stimulation location is determined. The first electromagnetic effect is induced by a first electrical quantity assigned to a first current element at a first current element location with a first orientation. A second electromagnetic effect at the stimulation location is also determined. The second electromagnetic effect is induced by a second electrical quantity assigned to a second current element at the first current element location with a second orientation. Based on the first electromagnetic effect and the second electromagnetic effect, an optimal orientation of a current element at the first current element location is determined. The orientation is such that the constraint is satisfied.

An exemplary computer-readable medium is also provided. The computer-readable medium has computer-readable instructions stored thereon that, upon execution by a processor, cause the processor to generate an optimal coil shape for magnetic stimulation. The instructions are configured to model a stimulation location based on an electrical property of the stimulation location. The instructions are also configured to determine a first electromagnetic effect at the stimulation location and a second electromagnetic effect at the stimulation location. The first electromagnetic effect is induced by a first electrical quantity assigned to a first current element. The first current element is at a first current element location with a first orientation. The second electromagnetic effect is induced by a second electrical quantity assigned to a second current element. The second current element is at the first current element location with a second orientation. The instructions are further configured to determine an optimal orientation of a current element at the first current element location based on the determined first electromagnetic effect and the determined second electromagnetic effect. The orientation is such that a constraint at the stimulation location is satisfied.

A second exemplary method of determining an optimal magnetic coil shape for use in magnetic stimulation is also provided. A model of at least a portion of a body part is generated based on an electrical property of the body part. The portion of the body part includes a stimulation location. A first electromagnetic effect at the stimulation location is determined using the model and a first electrical quantity assigned to a first current element at a first current element location with a first orientation. A second electromagnetic effect at the stimulation location is also determined using the model and a second electrical quantity assigned to a second current element at the first current element location with a second orientation. A first weighting factor corresponding to the first electromagnetic effect and a second weighting factor corresponding to the second electromagnetic effect are determined using a method of Lagrange multipliers. An overall weighting vector based on the first weighting factor and the second weighting factor is also determined. A direction component of the overall weighting vector comprises an optimal orientation of a current element at the first current element location such that a constraint at the stimulation location is satisfied.

Other principal features and advantages will become apparent to those skilled in the art upon review of the following drawings, the detailed description, and the appended claims.

BRIEF DESCRIPTION OF THE DRAWINGS

Exemplary embodiments will hereafter be described with reference to the accompanying drawings.

DETAILED DESCRIPTION

Figure 1:
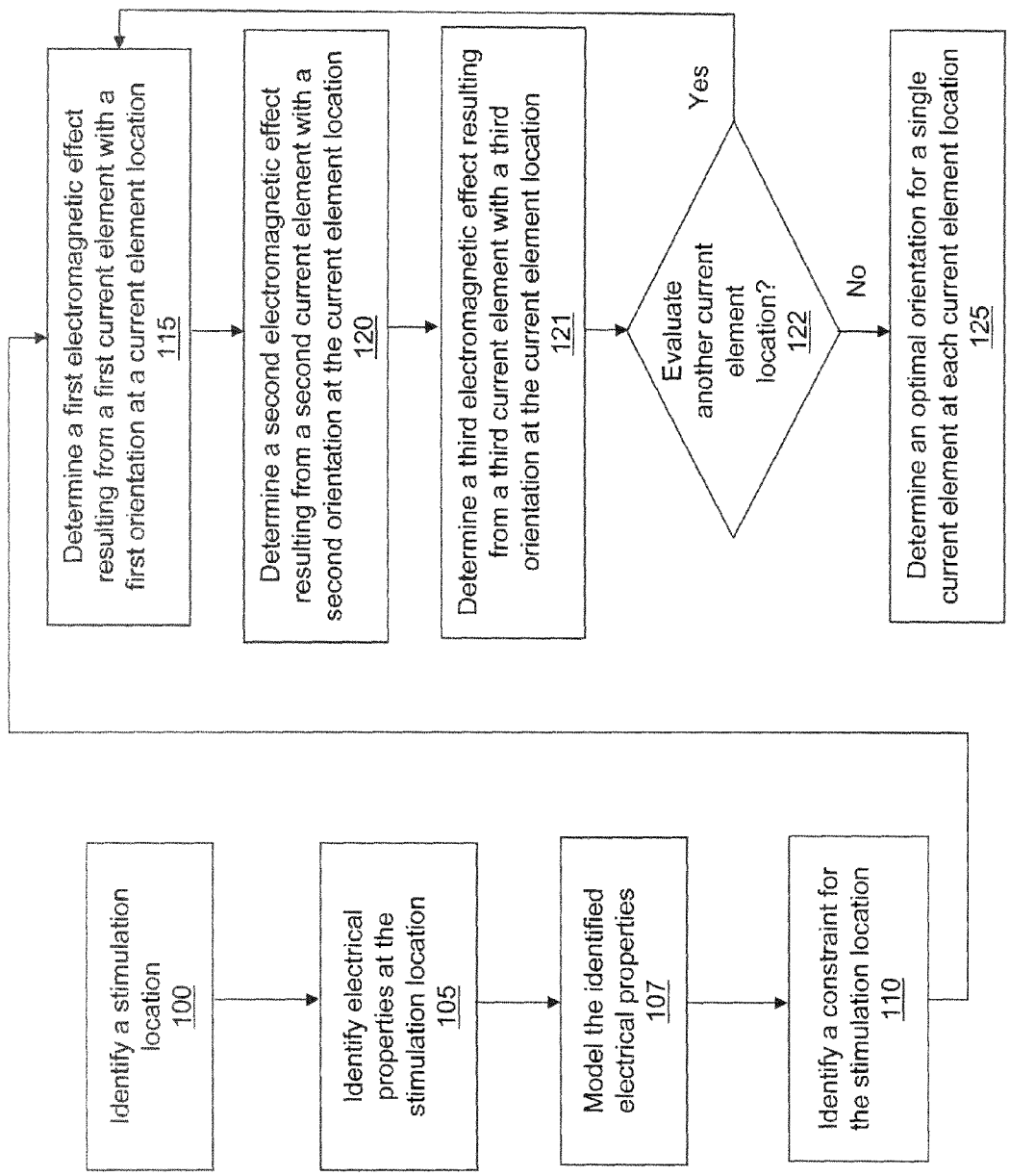
FIG. 1 is a flow diagram illustrating operations performed to determine an optimal magnetic stimulation coil shape in accordance with an exemplary embodiment.

FIG. 1 is a flow diagram illustrating operations performed to determine an optimal magnetic stimulation coil shape in accordance with an exemplary embodiment. Additional, fewer, or different operations may be performed in alternative embodiments. In an exemplary embodiment, any of the operations described with reference to FIG. 1 can be performed through a computer simulation, with any other computer software, with hardware, and/or manually. Once determined, the optimal magnetic stimulation coil shape can be used as a guide in the construction of an optimal magnetic stimulation coil. The optimal magnetic stimulation coil can be used in a magnetic stimulation device to provide magnetic stimulation to a patient. As used herein, magnetic stimulation can refer to a depolarizing stimulus applied to neural or any other tissue, a hyperpolarizing stimulus applied to neural or any other tissue, any magnetic stimulus applied to a bone fracture to enhance healing, or any other magnetic energy applied to a patient or other individual through a magnetic field. In one embodiment, magnetic stimulation can be used to reduce specific absorption rates of harmful electromagnetic energy by reducing induced currents in specific locations due to electrical appliances, power lines, magnetic article surveillance scanners, etc.

In an operation 100, a stimulation location is identified. The stimulation location can be the location of any neural (or other) tissue in which magnetic stimulation is desirable. The neural tissue can be part of any nerve in a central or peripheral nervous system. For example, the stimulation location can be a specific location within a brain, a specific location in an ulnar nerve, a specific location in a spinal cord, a specific location in a thoracic nerve, a specific location in a sciatic nerve, a specific location in a femoral nerve, etc. Alternatively, the stimulation location can be any other tissue or bone location within a body. In one embodiment, the stimulation location can refer to the location of tissue or bone within an animal.

In an exemplary embodiment, it is desirable to design an optimal magnetic coil which can accommodate a wide array of patients. However, a particular stimulation location may vary from individual to individual. For example, the stimulation location may be a precise location along the ulnar nerve at which magnetic stimulation can be used to help treat an arm disorder. A patient A can be a petite woman in which the stimulation location is eight millimeters (mm) below the surface of the skin. A patient B can be a large man in which the stimulation location is thirty mm below the surface of the skin. As such, an optimal magnetic coil for magnetic stimulation in patient A may differ at least in size from an optimal magnetic coil for magnetic stimulation in patient B. In an exemplary embodiment, the optimal magnetic coil can be based on a stimulation location within an average human body. Alternatively, the optimal magnetic coil can be based on a stimulation location within a small human body, a large human body, an extra large human body, etc. In another alternative embodiment, the optimal magnetic coil can be based on the body of a specific patient.

In an exemplary embodiment, a plurality of stimulation locations can be identified such that magnetic stimulation can be simultaneously administered in a plurality of locations. For example, it may be desirable to apply a depolarizing stimulus at a first stimulation location along an ulnar nerve while simultaneously applying a hyperpolarizing stimulus at a second stimulation location along the ulnar nerve. Any number of stimulation locations can be identified for simultaneous magnetic stimulation, including two, three, four, five, etc. In an alternative embodiment, a single stimulation location may be identified. The stimulation locations can be identified by any method known to those of skill in the art.

Neural tissue, bone, bodily fluids, muscle, skin, and any other materials at or near the stimulation location can exhibit electrical properties which can affect the magnetic stimulation. In an operation 105, electrical properties at the stimulation location are identified. The electrical properties can include a resistance at the stimulation location, a reactance at the stimulation location, or any other electrical property which is capable of effecting a current through the stimulation location. In an exemplary embodiment, electrical properties of an area surrounding the stimulation location can also be identified. For example, if the stimulation location is within a body part such as an arm, electrical properties of the entire arm can be identified. The electrical properties of the stimulation location and the area surrounding the stimulation location can be identified by any method known to those of skill in the art.

In an operation 107, the identified electrical properties are modeled. The electrical properties can be modeled by a computer as a simulation of the stimulation location(s) and the materials by which they are surrounded. Alternatively, the electrical properties can be physically modeled within a body part replica. In an exemplary embodiment, the electrical properties can be represented as circuit elements in an electrical model such as a circuit diagram. Alternatively, the electrical properties can be represented by any other type of model, equation(s), data, etc. known to those skilled in the art. In one embodiment, a low frequency impedance method can be used to model the stimulation location and surrounding area. The low frequency impedance method assumes a low (less than approximately one hundred kilohertz) frequency in the magnetic stimulation pulse and the resulting eddy currents at and around the stimulation location(s) such that the reactive component of impedance at and around the stimulation location(s) can be ignored. As such, the impedance at the stimulation location(s) can be represented with resistive elements.

Figure 2A:
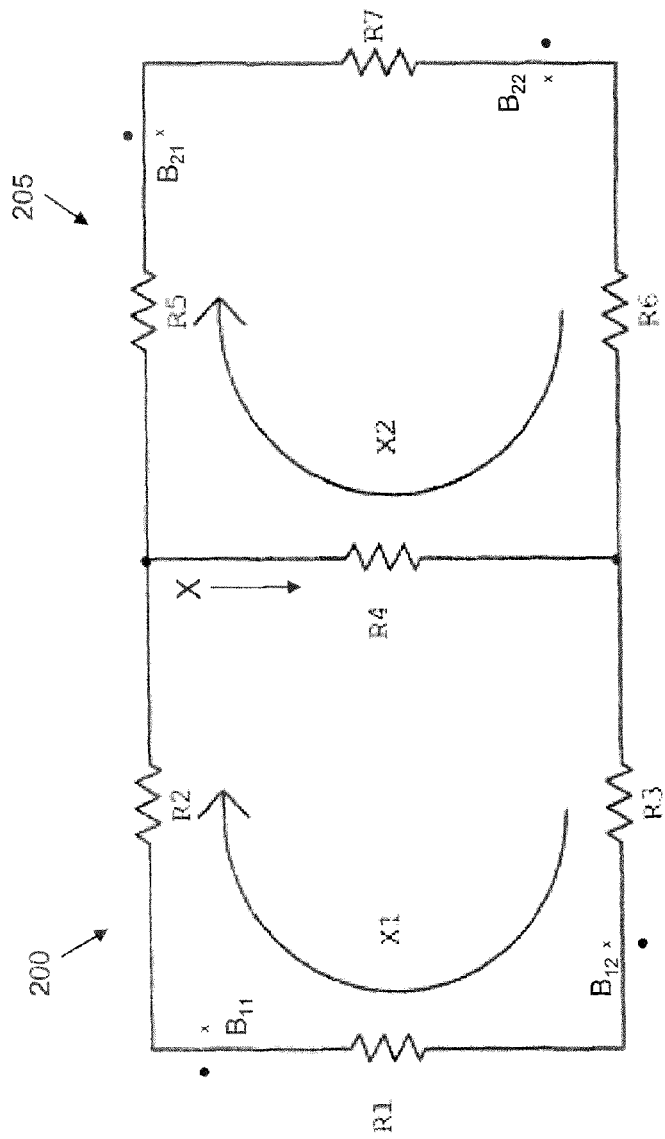
FIG. 2A is a circuit diagram illustrating electrical properties at and around a stimulation location in accordance with an exemplary embodiment.

FIG. 2A is a circuit diagram illustrating electrical properties at and around a stimulation location in accordance with an exemplary embodiment. The circuit diagram is a two dimensional representation which includes a first loop face 200 and a second loop face 205. In alternative embodiments, any other number of loop faces can be used. For example, one or more additional loop faces can be included to the left of the first loop face 200, above the first loop face 200, below the first loop face 200, above the second loop face 205, below the second loop face 205, to the right of the second loop face 205, in front of the first loop face 200 and/or second loop face 205 such that the model is three dimensional, behind the first loop face 200 and/or the second loop face 205 such that the model is three dimensional, and/or in any other positions such that the area at and around the stimulation location can be adequately modeled. In an alternative embodiment, reactance, inductance, capacitance, and/or any other electrical properties can also be represented in the circuit diagram. In another alternative embodiment, the loop faces can modeled as any other shape(s) and/or size(s). For example, a loop face which is close to the stimulation location may be smaller than a loop face which is far from the stimulation location such that greater resolution is achieved at and near the stimulation location.

Figure 2B:
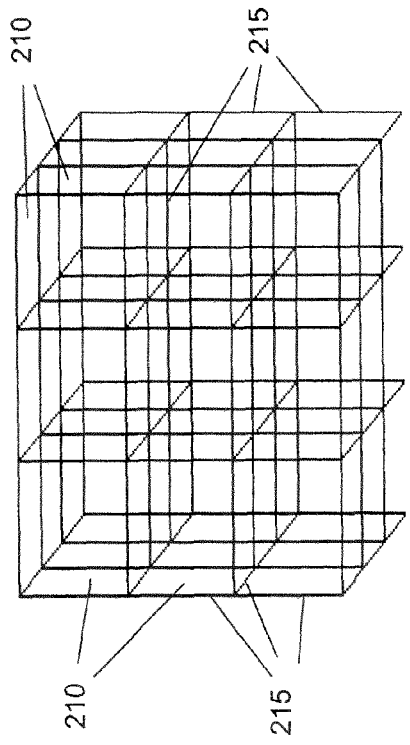
FIG. 2B is a three dimensional cube diagram for representing electrical properties at and around a stimulation location in accordance with an exemplary embodiment.

The first loop face 200 has an eddy (or loop) current $X_1$ which runs through its resistive elements $R_1$, $R_2$, $R_3$, and $R_4$. Similarly, the second loop face 205 has an eddy (or loop) current $X_2$ which runs through its resistive elements $R_4$, $R_5$, $R_6$, and $R_7$. The eddy currents $X_1$ and $X_2$ can result from a time varying magnetic field caused by a time varying current in a magnetic coil placed near the stimulation location. In an exemplary embodiment, the values of the resistive elements can vary based on the material at and surrounding the stimulation location. For example, $R_4$ can correspond to a resistance of neural tissue at the stimulation location, $R_7$ can correspond to a resistance of solid bone near the stimulation location, $R_1$ can correspond to a resistance of blood near the stimulation location, etc. In an exemplary embodiment, the first loop face 200 and the second loop face 205 can correspond to any dimensions at the stimulation location. For example, each side of the first loop face 200 can be equivalent to a length of one micrometer (um) at the stimulation location, one mm at the stimulation location, five mm at the stimulation location, etc. In an alternative embodiment, a three dimensional circuit diagram can be used. FIG. 2B is a three dimensional cube diagram for representing electrical properties at and around a stimulation location in accordance with an exemplary embodiment. Each loop face 210 within the cube diagram can represent a current loop near the stimulation location, and each cube boundary 215 can include a resistive or other circuit element which represents an electrical property at or near the stimulation location.

Referring back to FIG. 1, a constraint for the stimulation location is identified in an operation 110. In an exemplary embodiment, the constraint can be a desired current flow through the stimulation location. For example, the constraint can be a specific value of a current X which flows through resistive element $R_4$ illustrated with reference to FIG. 2A. Alternatively, the constraint can be a desired electric field strength at the stimulation location, a desired electric field gradient at the stimulation location, a desired voltage at the stimulation location, etc. In an exemplary embodiment, a constraint can be identified for each identified stimulation location. For example, three stimulation locations may be identified for magnetic stimulation along the femoral nerve. A constraint at the first stimulation location can be a current of fifty milliamps (mA), a constraint at the second stimulation location can be a current of negative fifty mA, and a constraint at the third stimulation location can be a current of one hundred mA.

In one embodiment, one or more constraints can be used to ensure that other constraints are physically realizable. As an example, the relationship between the currents illustrated with reference to FIG. 2A is that current X equals loop current $X_1$ minus loop current $X_2$. Thus, it is not physically realizable to have constraints which require loop current $X_1$ to be fifty mA, loop current $X_2$ to be twenty mA, and current X to be one hundred mA. To prevent such a situation and ensure that the constraints are realizable, the above-described relationship between the currents can also be a constraint. In addition, constraints can be imposed as design considerations. For example, the constraint can be that Kirchhoff's current law is satisfied at each current element throughout the model such that a single wire can be used to construct the optimal magnetic coil. The constraints can be identified by any method known to those of skill in the art.

In an operation 115, a first electromagnetic effect resulting from a first current element with a first orientation at a current element location is determined. In an exemplary embodiment, the first current element can be physically or computer modeled as any structure capable of conducting a current. In another exemplary embodiment, the first current element can be modeled as a minute portion of the material to be used in constructing the optimal magnetic stimulation coil. For example, if the magnetic stimulation coil is to be constructed out of copper wire, the first current element can be modeled as a short piece of copper wire. Alternatively, the first current element can be modeled as any other shape and/or made from any other type of conducting material.

In an exemplary embodiment, the current element location can be any location near the skin surrounding the stimulation location. For example, the stimulation location can be a portion of the ulnar nerve located near the elbow. The current element location can be any location along the entire length of the arm or any other tissue at which a magnetic stimulation coil can be placed. The current element location can be adjacent to the surface of the skin, one mm from the surface of the skin, two mm from the surface of the skin, three mm from the surface of the skin, or any other distance from the surface of the skin such that a current element at that distance can generate an electromagnetic effect at the stimulation location without adversely affecting the skin. The first orientation can be any convenient orientation at the current element location in which the first current element can be placed.

In an exemplary embodiment, the first electromagnetic effect can be any effect resulting from an electrical quantity attributed or applied to the first current element. In another exemplary embodiment, the electrical quantity can be a current change with respect to time (di/dt) value. The di/dt value can be one amp/second (A/s), or any other di/dt value depending on the embodiment. In one embodiment, the same electrical quantity can be attributed to each current element used to model the magnetic coil. As an example, the electrical quantity attributed to the first current element can be a di/dt of one A/s, and the first electromagnetic effect can be an eddy current at the stimulation location resulting from the first current element. Alternatively, the first electromagnetic effect can be an electric field at the stimulation location, a magnetic flux at the stimulation location, an electric field gradient at the stimulation location, etc. In an exemplary embodiment, the first electromagnetic effect can also refer to an electromagnetic effect in the area surrounding the stimulation location. The first electromagnetic effect can be determined by any method known to those of skill in the art.

In an operation 120, a second electromagnetic effect resulting from a second current element with a second orientation at the current element location is determined. In an exemplary embodiment, the second current element can be physically or computer modeled as the same size, shape, material etc. as the first current element described with reference to operation 115. In another exemplary embodiment, the second orientation can be orthogonal to the first orientation. Alternatively, the second orientation can be any orientation which is not parallel to the first orientation and in which the second current element is not obstructed by the surface of the skin. The second electromagnetic effect can be an effect resulting from an electrical quantity attributed or applied to the second current element. The electrical quantity can be the same as or different from the electrical quantity attributed or applied to the first current element depending on the embodiment.

In an operation 121, a third electromagnetic effect resulting from a third current element with a third orientation at the current element location can be determined. The third orientation can be orthogonal to the first orientation and the second orientation. Alternatively, the third orientation can be any other orientation which does not lie in a plane formed by the first orientation and the second orientation. The third orientation can be used to determine an optimal orientation of a three dimensional current element at the current element location. In alternative embodiments, only two current elements may be used at any or all of the current element locations. If only the first and second orientations are used to determine the optimal orientation of a single current element at the current element location, the optimal orientation can correspond to a two dimensional current element. Alternatively, if it is known that the optimal orientation cannot lie in a given direction due to a physical barrier, the first and second orientations can be used to determine an optimal three dimensional current element which lies in the plane formed by the first orientation and the second orientation.

In an operation 122, a decision is made regarding whether to evaluate current elements at another current element location. As such, operations 115, 120, and/or 121 can be repeated for each of a plurality of current element locations. For example, in addition to a first current element location, electromagnetic effects can also be determined at a second current element location distinct from the first current element location. If two current elements are modeled at each current element location, a third electromagnetic effect can be the effect caused by a third current element with a third orientation at the second current element location, and a fourth electromagnetic effect can be the effect caused by a fourth current element with a fourth orientation at the second current element location. If three current elements are modeled at each current element location, a fourth electromagnetic effect can be the effect caused by a fourth current element with a fourth orientation at the second current element location, a fifth electromagnetic effect can be the effect caused by a fifth current element with a fifth orientation at the second current element location, and so on. Similarly, electromagnetic effects resulting from current elements at a distinct third current element location, a distinct fourth current element location, etc. can also be determined. This process can be repeated until any number of current element locations have been evaluated. In an exemplary embodiment, electromagnetic effects induced from a plurality of current element locations can be determined simultaneously.

Figure 3:
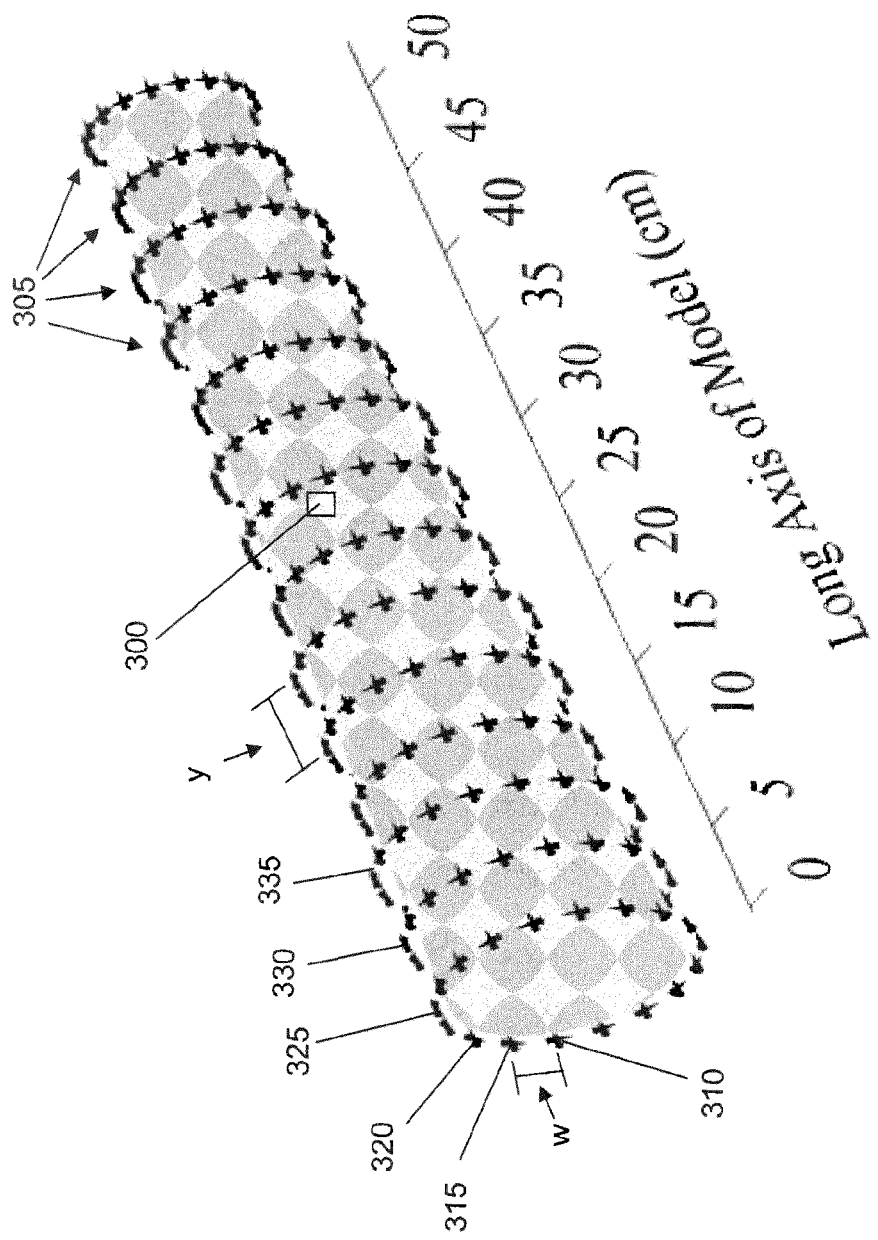
FIG. 3 is a location diagram illustrating a plurality of current element locations proximate to a stimulation location within an arm in accordance with an exemplary embodiment.

The plurality of current element locations can be selected randomly, uniformly, such that a pattern is formed, or based on any other criteria. In addition, each current element location within the plurality of current element locations can be any location in a three dimensional space surrounding the stimulation location in which the current element is not obstructed by the surface of the skin. FIG. 3 is a location diagram illustrating a plurality of current element locations proximate to a stimulation location 300 within an arm in accordance with an exemplary embodiment. In an exemplary embodiment, the stimulation location 300 can be a portion of an ulnar nerve located near an elbow of the arm. The current element locations are arrayed in a plurality of circular shapes 305 which surround the arm. The current element locations which make up each circular shape can be equidistant from one another, and the plurality of circular shapes 305 can be evenly spaced along the length of the arm. For example, a first current element location 310 can be a distance w from a second current element location 315, and the second current element location 315 can be the distance w from a third current element location 320, and so on. Similarly, a first circular shape 325 can be a distance y from a second circular shape 330, the second circular shape 330 can be the distance y from a third circular shape 335, and so on. In an exemplary embodiment, the distances w and y can be five mm. Alternatively, the distances w and y can be any other value(s). In another alternative embodiment, the plurality of current element locations can be arrayed in any other manner. For example, the current element locations can be randomly distributed about the stimulation location 300, in the shape of one or more spirals about the stimulation location 300, in the shape of one or more ovals about the stimulation location 300, etc.

Again referring back to FIG. 1, once the current element locations have been evaluated, an optimal orientation for a single current element at each current element location is determined in an operation 125. In an exemplary embodiment, the optimal orientation can be the orientation which satisfies the constraint(s), and which also results in a minimized root mean square (RMS) of the rate of change of current with respect to time (di/dt) in the current element. In an exemplary embodiment, the optimal orientations at a plurality of current element locations can be found simultaneously such that the RMS of di/dt is minimized at each of the plurality of current element locations. A high di/dt in a magnetic coil can correspond to an extremely high current through the magnetic coil. Such high current can cause the magnetic coil to overheat and/or adversely affect the resistance of the magnetic coil. Thus, a high di/dt can result in a magnetic coil which is not physically realizable or which has to be made of thick, heavy duty materials. Minimizing the RMS of di/dt can result in a magnetic coil with an efficient and realizable design.

In exemplary embodiment, the optimal orientation at each current element location can be determined by calculating one or more weighting factors capable of being applied to the determined electromagnetic effects. As described above, a first electromagnetic effect can be obtained by determining the effect at and around a stimulation location of an electrical quantity attributed to a first current element at a first current element location and with a first orientation. Similarly, a second electromagnetic effect can be obtained by determining the effect at and around the stimulation location of an electrical quantity attributed to a second current element at the first current element location and with a second orientation. A first weighting factor $m_1$ and a second weighting factor $m_2$ can be values by which the electrical quantity can be multiplied such that the overall electromagnetic effect of the first and second current elements at the first current element location corresponds to satisfying a constraint. The first and second weighting factors $m_1$ and $m_2$ can also be values by which the first electromagnetic effect and the second electromagnetic effect can be multiplied, respectively, such that the overall effect of the first and second current elements at the first current element location corresponds to satisfying a constraint.

As an example, a constraint can be a current of one hundred mA at a stimulation location. A di/dt of one A/s can be arbitrarily attributed to a first current element at a first current element location and with a first orientation and to a second current element at the first current element location and with a second orientation. A first electromagnetic effect can be an eddy current at the stimulation location resulting from the first current element with the first orientation, and a second electromagnetic effect can be an eddy current at the stimulation location resulting from the second current element with the second orientation. Using methods known to those of skill in the art, the first electromagnetic effect and the second electromagnetic effect can be calculated. Weighting factors $m_1$ and $m_2$ can be values by which the di/dt value assigned to the current elements with the first and second orientations should be multiplied, respectively, such that the overall effect of the two current elements is a current of one hundred mA (i.e., the constraint) at the stimulation location. As such, $m_1$ and/or $m_2$ can be less than, greater than, or equal to one. The weighting factors $m_1$ and $m_2$ can also be values by which the first electromagnetic effect and the second electromagnetic effect should be multiplied, respectively, such that the overall effect of the first and second current elements is a current of one hundred mA.

In one embodiment, a di/dt can also be assigned to a third current element at the first current element location and with a third orientation. The third orientation can be orthogonal to the first orientation and the second orientation. As such, a third weighting factor $m_3$ can correspond to the third current element at the first current element location with the third orientation. Weighting factors $m_1$, $m_2$, and $m_3$ can be the values by which the assigned di/dt value can be multiplied such that the overall effect of the three current elements corresponds to satisfying the constraint. Weighting factors $m_1$, $m_2$, and $m_3$ can also be values by which the first electromagnetic effect, the second electromagnetic effect, and a third electromagnetic effect should be multiplied, respectively, such that the overall effect of the first, second, and third current elements is a current of one hundred mA.

In an exemplary embodiment, weighting factors can be determined for each of a plurality of current element locations. For example, if two current elements are used at each current element location, weighting factors $m_1$ and $m_2$ can correspond to a first current element location, weighting factors $m_3$ and $m_4$ can correspond to a second current element location, weighting factors $m_5$ and $m_6$ can correspond to a third current element location, and so on. In another exemplary embodiment, the value of each weighting factor can depend at least in part on the value of each of the other weighting factors such that the combined effect of the weighting factors results in one or more constraints at one or more stimulation locations. As an example, if only three current element locations are used, the weighting factors $m_1$-$m_6$ can be the values by which a first electromagnetic effect, a second electromagnetic effect, a third electromagnetic effect, a fourth electromagnetic effect, a fifth electromagnetic effect, and a sixth electromagnetic effect should be multiplied, respectively, such that the overall effect of the current elements at the first, second, and third current element locations satisfies a constraint at a stimulation location.

In an exemplary embodiment, the weighting factors can be combined with one another using vector addition such that an overall weighting vector M can be determined. The overall weighting vector M can be a vector which represents the magnitude and orientation of an optimally placed current element at a current element location. For example, if two current elements with orthogonal orientations are used at the current element location, the overall weighting vector M can be equal to the square root of the sum of $m_1^2$ and $m_2^2$ ($\sqrt{m_1^2+m_2^2}$). If three current elements with orthogonal orientations are used, the overall weighting vector M can be equal to the square root of the sum of $m_1^2$, $m_2^2$ squared, and $m_3^2$ ($\sqrt{m_1^2+m_2^2+m_3^2}$). In an exemplary embodiment, an overall weighting vector M can be calculated for each stimulation location such that the orientation and magnitude of a plurality of optimally placed current elements can be determined.

In an exemplary embodiment, a set of two ($m_1$ and $m_2$) or three ($m_1$, $m_2$, and $m_3$) individual weighting factors can be determined for each current element location. Each set of individual weighting factors can be used to determine the overall weighting vector M for each current element location. For example, weighting factors $m_1$ and $m_2$ can correspond to two current elements at orthogonal orientations at a first current element location. Weighting factors $m_1$ and $m_2$ can be combined to determine an optimal current element orientation at the first current element location in the form of overall weighting vector $M_1$. Similarly, weighting factors $m_3$ and $m_4$ can correspond to two current elements with orthogonal orientations at a second current element location. Weighting factors $m_3$ and $m_4$ can be combined to determine an optimal current element orientation at the second current element location in the form of an overall weighting vector $M_2$. As such, $M_1$, $M_2$, $M_3$, ... $M_p$ can be determined, where $M_p$ is an optimal orientation for a single current placed at current element location p. In an exemplary embodiment, p can be any value, including ten, one hundred, one thousand, ten thousand, etc. The current element orientations obtained from the M values can be combined to form an optimal shape of a magnetic coil for magnetic stimulation at the stimulation location.

In another exemplary embodiment, the individual weighting factors $m_1$, $m_2$, $m_3$, $m_4$, $m_5$, etc. can be determined using the method of Lagrange multipliers as known to those skilled in the art. The method of Lagrange multipliers can be used to ensure that the sum of the squares of the individual weighting factors is minimized. If the sum of the squares of the individual weighting factors is minimized, it follows that the square root of the mean of the sum of the squares is also minimized. Thus, the RMS of di/dt is minimized.

What follows is a simplified example for determining an optimal current element orientation at a single current element location. Electrical properties of a stimulation location can be represented by the circuit diagram illustrated with reference to FIG. 2A. The current element location can include a first current element with a first orientation and a second current element with a second orientation. The first orientation and the second orientation can be orthogonal to one another. Both the first current element and the second current element can be assigned a di/dt value of one A/s. A single constraint can be that the current X in FIG. 2A be equal to one hundred mA.

In an exemplary embodiment, with a di/dt of one A/s, the first current element can cause a time varying magnetic flux $B_{11}$ through the first loop face 200 of the circuit diagram. The first current element can also cause a time varying magnetic flux $B_{21}$ through the second loop face 205 of the circuit diagram. Likewise, the second current element can cause a time varying magnetic flux $B_{12}$ through the first loop face 200, and a time varying magnetic flux $B_{22}$ through the second loop face 205. In an exemplary embodiment, the magnetic flux can be a measure of the strength of the magnetic field over an area of a loop face. The time varying magnetic flux values can be calculated by using the assigned di/dt value (or any other assigned electrical quantity), the area of the loop face, and the Biot-Savart law as known to those skilled in the art. Alternatively, the time varying magnetic flux can be determined using physically measured electromagnetic properties, or by any other method known to those of skill in the art.

In an exemplary embodiment, the time varying magnetic flux values can be used along with the values of the resistive elements to calculate the loop (or eddy) currents $X_1$ and $X_2$ resulting from the first current element and the second current element. In another exemplary embodiment, the loop currents $X_1$ and $X_2$ can be calculated using an impedance matrix equation. Equation 1 below is an exemplary impedance matrix equation corresponding to the first current element. In Equation 1, $R_1$-$R_7$ are resistance values corresponding to resistive elements $R_1$-$R_7$, $X_{11}$ is a loop current in the first loop face 200 caused by the first current element, $X_{21}$ is a loop current in the second loop face 205 caused by the first current element, $B_{11}$ is the time varying magnetic flux caused by the first current element in the first loop face 200, and $B_{21}$ is the time varying magnetic flux caused by the first current element in the second loop face 205. Equation 1 can be solved by matrix inversion, iteration, or any other method known to those of skill in the art such that the loop currents $X_{11}$ and $X_{21}$ can be determined.

$$\begin{bmatrix} (R_1+R_2+R_3+R_4) & -R_4 \\ -R_4 & (R_4+R_5+R_6+R_7) \end{bmatrix} \begin{bmatrix} X_{11} \\ X_{12} \end{bmatrix} = \begin{bmatrix} -B_{11} \\ -B_{21} \end{bmatrix} \quad \text{Equation 1}$$

Equation 2 below is an exemplary impedance matrix equation corresponding to the second current element. In Equation 2, $X_{12}$ is a loop current in the first loop face 200 caused by the second current element, $X_{22}$ is a loop current in the second loop face 205 caused by the second current element, $B_{12}$ is the time varying magnetic flux caused by the second current element in the first loop face 200, and $B_{22}$ is the time varying magnetic flux caused by the second current element in the second loop face 205.

$$\begin{bmatrix} (R_1+R_2+R_3+R_4) & -R_4 \\ -R_4 & (R_4+R_5+R_6+R_7) \end{bmatrix} \begin{bmatrix} X_{12} \\ X_{22} \end{bmatrix} = \begin{bmatrix} -B_{12} \\ -B_{22} \end{bmatrix} \quad \text{Equation 2}$$

In an exemplary embodiment, a first electromagnetic effect can be a value of current through tissue caused by the first current element. Similarly, a second electromagnetic effect can be the same or a different value of current through tissue caused by the second current element. Alternatively, the first and/or second electromagnetic effects can refer to the time varying magnetic fluxes and/or the loop currents caused by the first and second current elements. In another exemplary embodiment, the values of current through the tissue caused by the first and second current elements can be determined by using a constraint equation based on the relationship of the loop currents and the desired current through the tissue. For example, as known to those of skill in the art, the current through the tissue is equal to loop current $X_1$ minus loop current $X_2$. This relationship can be illustrated as the matrix constraint equation of Equation 3 below.

$$[1 \quad -1] \begin{bmatrix} X_1 \\ X_2 \end{bmatrix} = X \quad \text{Equation 3}$$

In an exemplary embodiment, a first weighting factor $m_1$ can correspond to the first electromagnetic effect and a second weighting factor $m_2$ can correspond to the second electromagnetic effect. The relationship between the weighting factors and the electromagnetic effects can be illustrated in matrix form in Equation 4 below. In Equation 4, the value of the current X is set to the constraint value of one hundred mA. This relationship is illustrated in expanded form in Equation 5 below in which $X_{11}$-$X_{21}$ corresponds to the first electromagnetic effect and $X_{12}$-$X_{22}$ corresponds to the second electromagnetic effect.

$$[1 \quad -1] \begin{bmatrix} X_{11} & X_{12} \\ X_{21} & X_{22} \end{bmatrix} \begin{bmatrix} m_1 \\ m_2 \end{bmatrix} = X = 100 \text{ mA} \quad \text{Equation 4}$$

$$m_1(X_{11}-X_{21}) + m_2(X_{12}-X_{22}) = 100 \text{ mA} \quad \text{Equation 5}$$

It can be seen from Equation 5 that the first and second weighting factors $m_1$ and $m_2$ are values by which the first electromagnetic effect and the second electromagnetic effect can be multiplied, respectively, such that the constraint is satisfied. Equation 5 is one equation with two unknowns such that infinitely many solutions for $m_1$ and $m_2$ are available. Thus, it is desirable to identify a particular solution for $m_1$ and $m_2$ such that an optimal current element orientation and magnitude can be determined at the current element location. As described above, $m_1$ and $m_2$ can be related to one other as illustrated by Equation 6 below in which M is an overall weighting vector for the current element location. Further, it can be shown that the solution of $m_1$ and $m_2$ which results in a minimized $M^2$ also results in a minimized RMS of the di/dt values at all of the current element locations. Thus, the solution of $m_1$ and $m_2$ in which $M^2$ is minimized can also be the solution which provides an optimal orientation and magnitude for a single current element at the current element location.

$$M = \sqrt{m_1^2 + m_2^2} \Rightarrow M^2 = m_1^2 m_2^2 \quad \text{Equation 6}$$

In an exemplary embodiment, the method of Lagrange multipliers can be used to establish a linear set of equations to solve for values of $m_1$ and $m_2$ such that $M^2$ is minimized. Equation 7 below, in which A is a Lagrange multiplier, illustrates the method of Lagrange multipliers in matrix form. Equation 7 can be solved, and the values of $m_1$ and $m_2$ determined, by using matrix inversion, iteration, or any other method known to those of skill in the art. The calculated values of $m_1$ and $m_2$ can be used to calculate the overall weighting vector M. The overall weighting vector M can be a vector representing the optimal orientation and magnitude of a single current element placed at the current element location. In an exemplary embodiment, when a plurality of current element locations are used, Equation 7 can be used to simultaneously determine all of the individual weighting factors.

$$\begin{bmatrix} 2 & 0 & (X_{11} - X_{21}) \\ 0 & 2 & (X_{12} - X_{22}) \\ (X_{11} - X_{21}) & (X_{12} - X_{22}) & 0 \end{bmatrix} \begin{bmatrix} m_1 \\ m_2 \\ -\lambda \end{bmatrix} = \begin{bmatrix} 0 \\ 0 \\ X \end{bmatrix} \quad \text{Equation 7}$$

In an exemplary embodiment, the matrices in Equation 7 can take a general form such that weighting factors corresponding to a plurality of current element locations can be simultaneously determined. For example, the left-most matrix can be a square matrix of n+k rows and n+k columns, where n is the number of current elements used and k is the number of constraints. In the example above, there were two current elements used such that n equals two and a single constraint (current X equal to one hundred mA) such that k equals one. In addition, the first n rows and n columns can be a diagonal matrix with twos on the main diagonal (and zeros elsewhere). The matrix elements in the last k rows and the first n columns can be obtained by performing matrix multiplication of the two left-most matrices of Equation 4 (which can include one entry corresponding to each current element at each current element location). The matrix elements in the first n rows and the last k columns can be the transpose of the matrix elements in the last k rows and the first n columns. Lastly, the matrix elements corresponding to the last k rows and k columns can include zeros. The middle matrix of Equation 7 can include n individual weighting factors ($m_1$, $m_2$, $m_3$, ..., $m_n$) followed by k Lagrange multipliers ($\lambda_1$, $\lambda_2$, ..., $\lambda_k$). The right-most matrix of Equation 7 can include n zeros followed by k constraint values. In an exemplary embodiment, individual rows or columns of the matrix can be multiplied by any scalar to simplify solving the matrix and/or to improve the accuracy of the matrix solution.

In an exemplary embodiment, the equations described above can be used to determine optimal current element orientations and magnitudes at a plurality of current element locations such that an optimal magnetic coil shape can be determined. As an example, two hundred fifty current element locations can be selected around a stimulation location. Three current elements can be modeled (or physically placed) at each of the two hundred fifty current element locations such that seven hundred fifty current elements are modeled. A first current element at a first current element location can have a first orientation, a second current element at the first current element location can have a second orientation, and a third current element at the first current element location can have a third orientation. In an exemplary embodiment, the first orientation, the second orientation, and the third orientation can all be orthogonal to one another. Similarly, a fourth current element at a second location can have a fourth orientation, a fifth current element at the second location can have a fifth orientation, and a sixth current element at the second location can have a sixth orientation. The fourth, fifth, and sixth orientations can be orthogonal to one another, and may or may not correspond to the first, second, and third orientations. In an exemplary embodiment, the current elements can be modeled in a computer simulation such that a computer can determine electromagnetic effects caused by each current element at and around the stimulation location. In an alternative embodiment, the current elements can be physically placed around a body part or body part replica such that actual measurements of the electromagnetic effects within the body part or body part replica can be made.

In one embodiment, the body part within which the stimulation location is located can be physically or computer modeled based on electrical properties of the body part. For example, the body part can be modeled as a plurality of cubes with cube faces as illustrated with reference to FIG. 2B. Each cube edge can include one or more circuit elements such as resistors, inductors, capacitors, etc. which represent the electrical properties of the body part. Alternatively, the body part can be modeled as equations, data, or by any other method capable of conveying electrical properties of the body part. In another exemplary embodiment, an electrical quantity of $di/dt = 1$ A/s can be attributed or applied to each of the seven hundred fifty modeled current elements. In an alternative embodiment, any other value of di/dt can be used.

In an exemplary embodiment, an impedance matrix equation can be used to simultaneously determine an electromagnetic effect caused by each current element within the body part. Alternatively, any other type of equation or method can be used to determine the electromagnetic effects. The electromagnetic effects can be determined at a plurality of locations at and surrounding the stimulation location. In an exemplary embodiment, the electromagnetic effects can be determined at each location within the body part model. For example, if the body part model is a plurality of cubes, the current generated at each cube edge can be determined by calculating the time varying magnetic flux through each cube face within the plurality of cubes.

In another exemplary embodiment, there can be a single constraint of an electric field gradient of forty Volts per square meter ($V/m^2$) at the stimulation location. One or more constraint equations can be formed such that the electromagnetic effect(s) can be represented in terms of the constraint. The method of Lagrange multipliers as illustrated with reference to Equation 7 can be used to simultaneously determine seven hundred fifty individual weighting coefficients such that an overall weighting coefficient corresponding to each current element location is minimized. The seven hundred fifty weighting coefficients can be grouped into sets of three where each set corresponds to the three current elements at a single current element location. The three current elements in each set can be used to determine the overall weighting vector for each current element location such that an optimal orientation and magnitude at that current element location is obtained. The optimal orientation at each of the current element locations can be combined such that an optimal shape for a magnetic coil is provided.

Experimental Data

In an experiment conducted using the above-described methods, an optimized magnetic coil was designed for use with a replica of an average adult human right arm. An optimal magnetic coil shape was determined using a computer simulated arm. The optimal magnetic coil shape was used to build an optimal magnetic coil. In addition, the optimal magnetic coil was evaluated by taking measurements along a physical arm replica of the simulated arm around which the optimal magnetic coil was placed.

The computer simulated arm was a tapered cylinder with a 30 cm circumference at its large end and a 20 cm circumference at its small end. The total length of the simulated arm was 52 centimeters (cm), representing an average adult human arm from the shoulder to the wrist. For computational purposes, the simulated arm was encased in a volume of 10 cm×10 cm×52 cm. 'Air' cells having zero conductivity were placed around the rectangular volume to yield a model with a tapered cylindrical shape. Each side of each cube was modeled as a loop face having sides of 5 mm in length. Cubes and portions thereof which were outside of the simulated arm were eliminated such that the remaining cubes conformed to the shape of the tapered cylinder.

Figure 4:
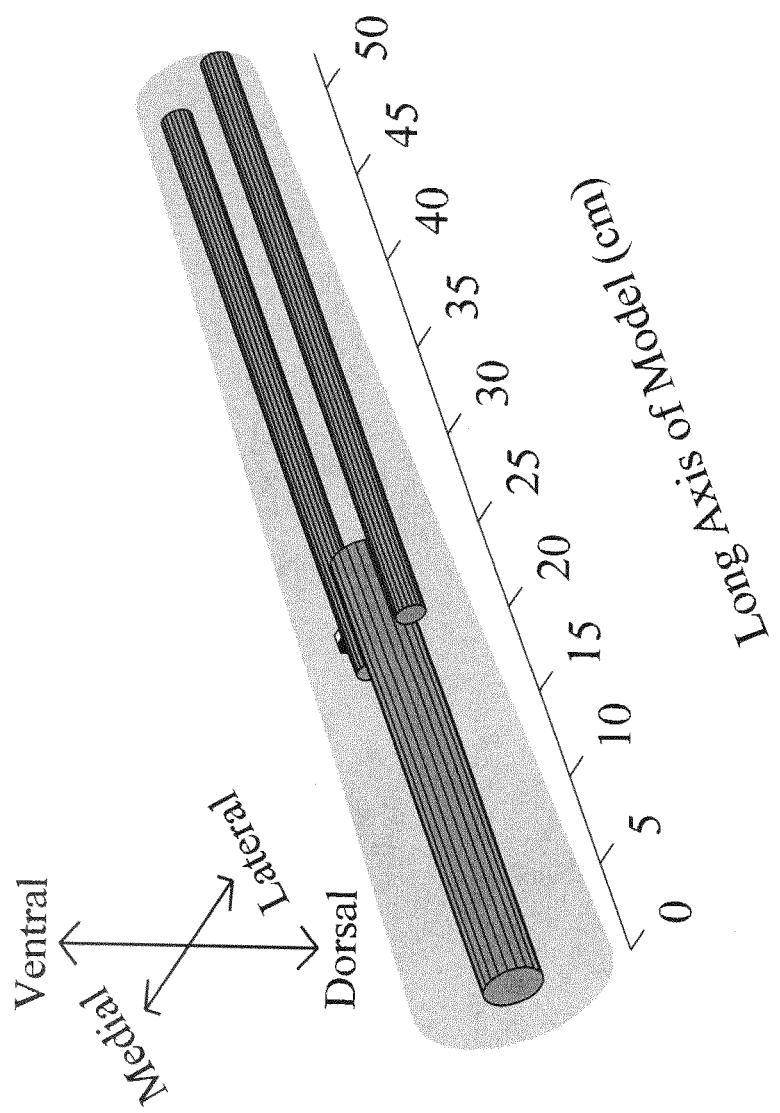
FIG. 4 illustrates a simulated arm in accordance with an exemplary embodiment.

Within the simulated arm were three cylinders to represent the humerus, radius, and ulna. The cylinder representing the humerus was 25 cm long and 3 cm in diameter. The cylinders representing the radius and ulna were each 32 cm long and 1.5 cm in diameter. The three cylinders were placed within the tapered cylinder in an arrangement similar to that of the human arm, and were allowed to overlap by about 5 cm to represent the enlarged bony areas of the humerus and ulna near the elbow. The simulated arm was given conductivity values similar to that for bone (0.02 S/m at 1300 Hz) in the cylinders and similar to that for muscle (0.32 S/m at 1300 Hz) everywhere else. These conductivity values were used to model the electrical properties along each loop face within the plurality of cubes representing the simulated arm. It was assumed that all muscle fibers were oriented along the long axis of the simulated arm. FIG. 4 illustrates the simulated (and replica) arm in accordance with an exemplary embodiment.

Two hundred fifty-two current element locations were selected around the simulated arm. The current element locations were selected to totally surround the simulated arm such that no presuppositions were made concerning the ultimate shape of the optimal magnetic coil. The current element locations were arranged as rings about the simulated arm with each of the current element locations within a ring equidistantly spaced from one another. A distance of 4 cm separated each ring, and the rings spanned the entire length of the simulated arm. Each current element location was located 5 mm outside the (skin) surface of the simulated arm.

Two current elements were modeled at each current element location. The first current element was oriented in the same direction as the long axis of the simulated arm, and the second current element was oriented perpendicular to the first current element and tangential to the surface of the simulated arm. Thus, a total of 504 current elements were modeled. The first current element was assigned a di/dt magnitude of 1 A/s, and the changing magnetic flux intersecting each loop face of each cube representing the simulated arm was calculated. The resulting interior eddy currents were found by solving an impedance matrix equation via the method of pre-conditioned conjugate gradients. The diagonal of the impedance matrix was used as a pre-conditioner in order to speed the processing. The pre-conditioned conjugate gradient algorithm was terminated when the relative error in the solution was less than $1 \times 10^{-6}$. The results were saved, and the process was repeated for each of the other 503 current elements.

Once all of the interior eddy currents resulting from the 504 current elements were determined, a first constraint equation was developed to specify a first constraint at a first stimulation location. The first constraint was a depolarizing stimulus of $-54$ V/m$^2$. The first stimulation location was located at 22.5 cm along the length of the simulated arm, 8.5 cm from the lateral (outside) edge of the simulated arm, and 5 cm from the dorsal (equivalent to the back side of the arm) edge of the simulated arm. The first stimulation location was meant to be at the medial side of the "elbow" near where the ulnar nerve would be located in a real arm. A second constraint equation was also developed to specify a second constraint at a second stimulation location. The second constraint was a hyperpolarizing stimulus of 54 V/m$^2$. The second stimulation location was located at 23 cm along the length of the simulated arm, 8.5 cm from the lateral edge of the simulated arm, and 5 cm from the dorsal edge of the simulated arm.

To ensure that the magnetic coil could be made from a single continuous conductor and be used with a single magnetic stimulator, an additional constraint was that Kirchhoff's current law be satisfied throughout the coil elements modeling the coil. As such, additional constraint equations were imposed to ensure that the constraints were met. In alternative embodiments, the magnetic coil may be made from a plurality of non-continuous conductors. Using the calculated eddy currents and the constraint equations, the method of Lagrange multipliers was employed to find the optimized orientation at each current element location. The method of Lagrange multipliers ensures that the design is globally optimal in terms of minimizing the RMS values of the di/dt magnitudes.

After analyzing the results, a number of simplifications were made prior to physically building the magnetic coil. The analysis showed that only the current elements within approximately 12 cm of the stimulation locations had any significant impact in controlling the stimulation. As such, the most proximal and distal current elements were eliminated to make the overall magnetic coil shape smaller. In addition, to facilitate measurements in a physical arm replica with a probe, several current elements near the medial surface of the stimulation locations were also eliminated. Further, even though Kirchhoff's current law was satisfied at every current element location, the magnitude values of di/dt were not all constant. A magnetic coil with varying di/dt values could have been implemented by splitting the current carrying conductor which makes up the magnetic coil and splicing it back together at various points to obtain the differing di/dts. However, such splitting and splicing may have been difficult to implement, and may also have uncontrollably altered the ultimate shape of the magnetic coil. As such, a single continuous conductor was used to build the magnetic coil such that all di/dts were forced to the same value. The shape of the magnetic coil was based on the calculated optimal orientations of current elements at each of the current element locations.

The magnetic coil was placed around a physical arm replica built to the same specifications as described with reference to the simulated arm. The physical replica was built of non-conductive and non-magnetic materials and filled with a 0.9% saline solution. The magnetic coil was pulsed with current delivered from a custom built magnetic stimulator. Two electrodes were used to take measurements of electric potential differences within the arm replica. The two electrodes were separated in the longitudinal direction by 5 mm and were inserted at a depth of about 1 cm into the saline of the arm replica. The electrodes were advanced in 1 cm increments along the length of the replica and the potential difference recorded at each location. The measurements were taken from 10 cm proximal to 10 cm distal to the stimulation locations. Measurements were also taken in this manner at locations 0.5 cm, 1.0 cm and 1.5 cm ventral and dorsal to the stimulation locations.

Figure 5A:
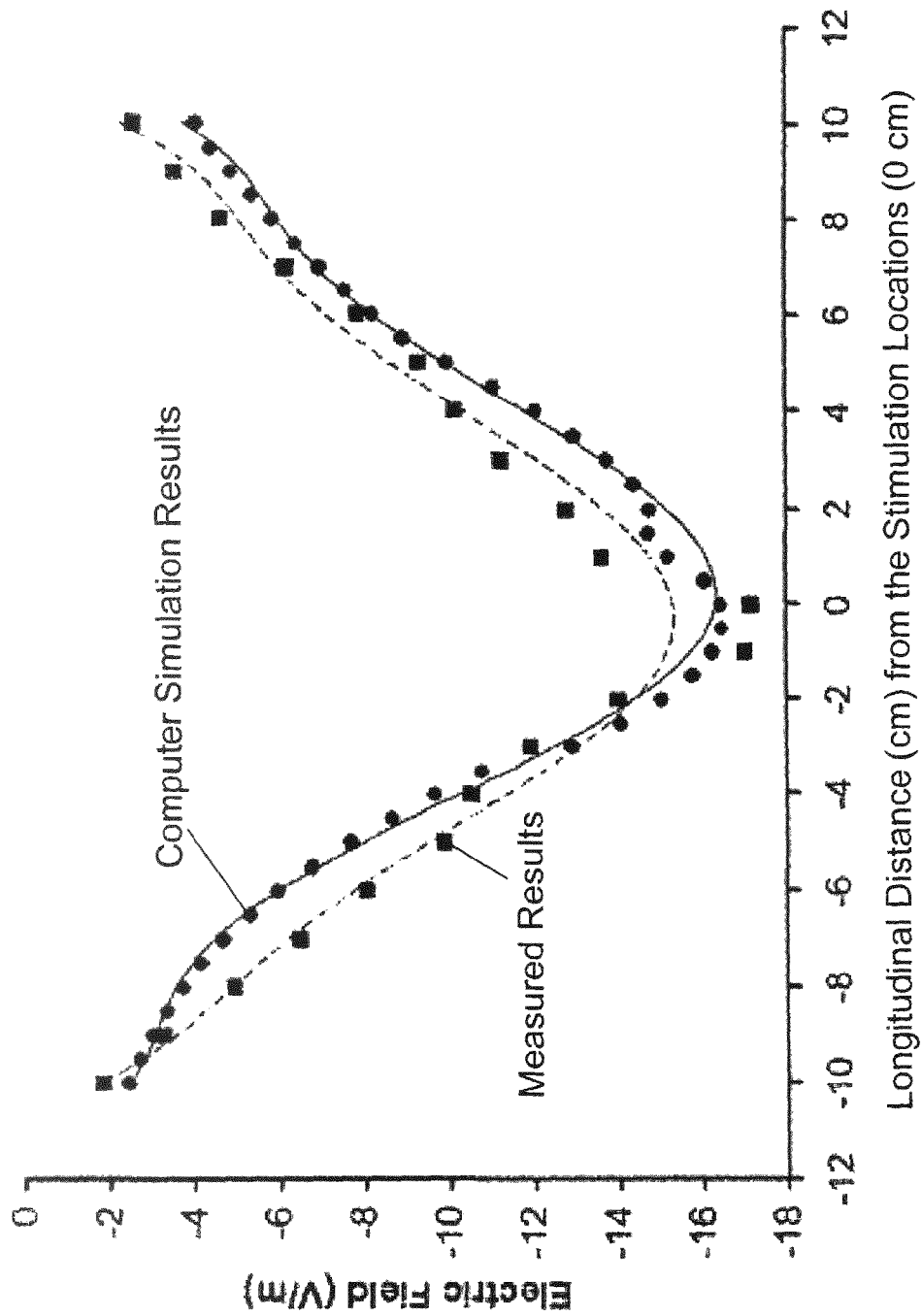
FIG. 5A is a graph comparing simulated and measured longitudinal electric fields obtained during a magnetic coil experiment in accordance with an exemplary embodiment.
Figure 5B:
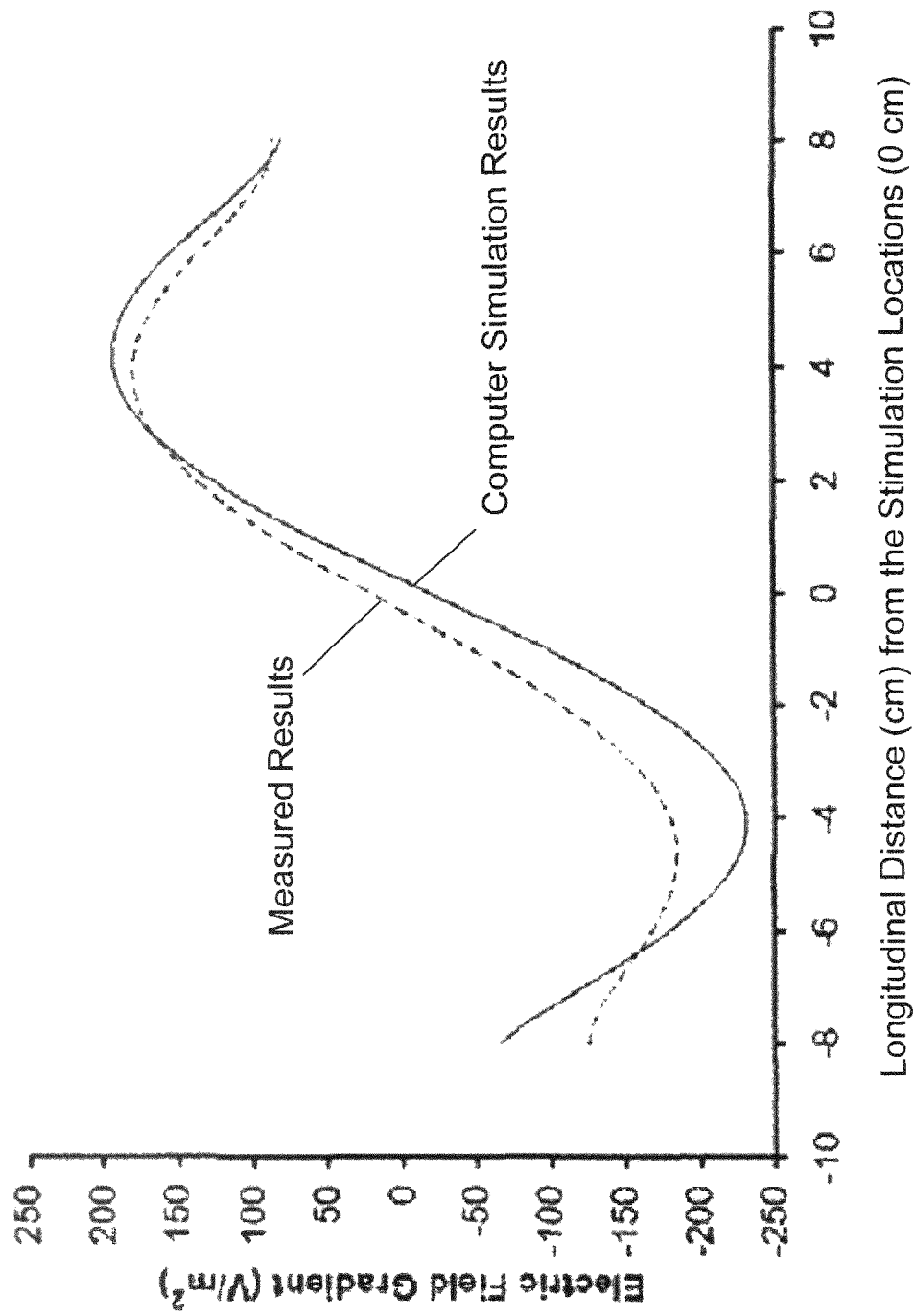
FIG. 5B is a graph comparing simulated and measured electric field gradients obtained during the magnetic coil experiment in accordance with an exemplary embodiment.

Using the measured values, the longitudinal electric field component from each of the potential difference measurements was calculated. A least squares polynomial of degree 6 was fit to the calculated electric field data and this polynomial was differentiated to provide the gradient of the electric field along the length of the replica. For comparison, a similar procedure was followed using the computer simulation data that was used to determine the optimal magnetic coil shape. The impedance method was used to find the eddy currents and the longitudinal electric field in the computer simulation. Further, just as was done with the measured data, the electric fields were examined at locations between 10 cm proximal and 10 cm distal to the stimulation locations and at points just ventral and dorsal to the stimulation locations. A least squares polynomial of degree 6 was fit to the average of the values based on the computer simulation. The derivative of this polynomial provided the gradients of the electric field along the length of the simulation. The squared correlation coefficient was then calculated between the gradients found from the simulation results and those found from the measured results. The squared correlation coefficient was found to be 0.97. FIG. 5A is a graph comparing the simulated and measured longitudinal electric fields as best fit polynomials in accordance with an exemplary embodiment. FIG. 5B is a graph comparing the simulated and measured electric field gradients in accordance with an exemplary embodiment. As illustrated with reference to FIG. 5B, the gradients within 0.5 to 1.0 cm of the stimulation locations were very near to the constraint values of ±54 V/m².

One or more flow diagrams have been used herein to describe exemplary embodiments. The use of flow diagrams is not meant to be limiting with respect to the order of operations performed. Further, for the purposes of this disclosure and unless otherwise specified, "a" or "an" means "one or more."

The foregoing description of exemplary embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of determining an optimal orientation of a current element of a magnetic coil for use in magnetic stimulation, the method comprising:
   (a) identifying a stimulation location;
   (b) identifying a constraint representing at least a desired electromagnetic effect at the stimulation location;
   (c) determining, by a processor of a computing device, a first electromagnetic effect at the stimulation location, wherein the first electromagnetic effect is induced by a first electrical quantity assigned to a first current element at a first current element location with a first orientation;
   (d) determining, by the processor of the computing device, a second electromagnetic effect at the stimulation location, wherein the second electromagnetic effect is induced by a second electrical quantity assigned to a second current element at the first current element location with a second orientation; and
   (e) determining, by the processor of the computing device, the optimal orientation of the current element at the first current element location based on the determined first electromagnetic effect and the determined second electromagnetic effect, wherein the optimal orientation is such that the constraint representing the desired electromagnetic effect is satisfied at the stimulation location;
   (f) repeating operations (c) and (d) at a second current element location to determine an optimal orientation of a current element at the second current element location; and (g) combining the determined orientation of the current element at the first current element location and the determined orientation of the current element at the second current element location to determine an optimal orientation of at least a portion of an array of stimulation current elements.

2. The method of claim 1, wherein the first electromagnetic effect is determined based at least in part on a time varying magnetic flux at the stimulation location.

3. The method of claim 1, wherein the first electromagnetic effect is determined by using an impedance equation.

4. The method of claim 1, wherein the first electromagnetic effect is determined by using a constraint equation based on the constraint.

5. The method of claim 1, further comprising determining a first weighting factor corresponding to the first electromagnetic effect and a second weighting factor corresponding to the second electromagnetic effect.

6. The method of claim 5, further comprising using vector addition to combine the first weighting factor and the second weighting factor to determine an overall weighting vector, wherein a direction component of the overall weighting vector comprises the orientation of the current element at the first current element location.

7. The method of claim 6, wherein the first weighting factor and the second weighting factor are determined using a method of Lagrange multipliers such that the overall weighting vector is minimized.

8. The method of claim 1, wherein the orientation of the current element at the first current element location is such that a rate of change of current with respect to time within the current element is minimized.

9. The method of claim 1, wherein the first electrical quantity and the second electrical quantity comprise a rate of change of current with respect to time value.

10. The method of claim 1, wherein the first electromagnetic effect comprises at least one of an eddy current, an electric field strength, and an electric field gradient.

11. The method of claim 1, wherein the first orientation and the second orientation are orthogonal to one another.

12. The method of claim 1, wherein the stimulation location comprises a location of tissue.

13. The method of claim 12, wherein the tissue comprises neural tissue.

14. The method of claim 1, wherein the stimulation location comprises a location of bone.

15. The method of claim 1, further comprising identifying an electrical property of the stimulation location.

16. The method of claim 15, wherein the electrical property of the stimulation location comprises a resistance.

17. The method of claim 15, wherein the first electromagnetic effect is determined based at least in part on the electrical property of the stimulation location.

18. The method of claim 15, further comprising modeling the stimulation location based on the identified electrical property.

19. The method of claim 1, further comprising determining, by the processor of the computing device, the first electromagnetic effect using a low frequency impedance method.

20. The method of claim 19, wherein a model of the stimulation location comprises a plurality of loop faces.

21. The method of claim 1, wherein the constraint comprises at least one of a desired current at the stimulation location, a desired electric field at the stimulation location, and a desired electric field gradient at the stimulation location.

22. The method of claim 1, wherein determining the orientation of the current element at the first current element location further comprises simultaneously determining the optimal orientation of the current element at the second current element location such that the constraint is satisfied.

23. The method of claim 1, wherein the first current element and the second current element are simulated at the first current element location.

24. The method of claim 1, wherein the first current element and the second element are physically located at the first current element location.

25. The method of claim 1, further comprising determining a third electromagnetic effect at the stimulation location, wherein the third electromagnetic effect is caused by a third electrical quantity assigned to a third current element at the first current element location with a third orientation, and further wherein the orientation of the current element at the first current element location is based on the determined first electromagnetic effect, the determined second electromagnetic effect, and the determined third electromagnetic effect.

* * * * *